(12) United States Patent
Ikenaga et al.

(10) Patent No.: US 12,152,232 B2
(45) Date of Patent: Nov. 26, 2024

(54) LACTOBACILLUS PARACASEI STRAIN

(71) Applicant: OTSUKA PHARMACEUTICAL CO., LTD., Tokyo (JP)

(72) Inventors: Takeshi Ikenaga, Osaka (JP); Tsuneyuki Noda, Osaka (JP); Yoshito Tajiri, Osaka (JP); Hiroki Noguchi, Osaka (JP); Atsushi Ueda, Osaka (JP); Noriyuki Kouda, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 15/921,174

(22) Filed: Mar. 14, 2018

(65) Prior Publication Data

US 2019/0055613 A1 Feb. 21, 2019

Related U.S. Application Data

(63) Continuation of application No. 15/127,301, filed as application No. PCT/JP2015/058750 on Mar. 23, 2015, now abandoned.

(30) Foreign Application Priority Data

Mar. 24, 2014 (JP) .................. 2014-060010

(51) Int. Cl.
A61K 35/747 (2015.01)
A23L 33/135 (2016.01)
C12N 1/20 (2006.01)
C12R 1/225 (2006.01)

(52) U.S. Cl.
CPC ............ C12N 1/205 (2021.05); A23L 33/135 (2016.08); A61K 35/747 (2013.01); C12N 1/20 (2013.01); *A23V 2002/00* (2013.01); *C12R 2001/225* (2021.05)

(58) Field of Classification Search
CPC .......... A01K 2217/075; A01K 2217/15; A01K 2227/105; A01K 2267/0331; A01K 2267/035; A01K 67/0276; A23L 33/135; A23V 2002/00; A61K 35/741; A61K 35/747; A61K 48/005; C07K 14/4702; C12N 15/8509; C12N 1/20; C12N 1/205; C12R 1/225; C12R 2001/225; G01N 2500/10; G01N 2800/065; G01N 2800/50; G01N 33/505; G01N 33/57419; G01N 33/6872
See application file for complete search history.

(56) References Cited

U.S. PATENT DOCUMENTS 8,637,297 B2 1/2014 Vieites Fernandez et al.
2011/0268702 A1 11/2011 Fukushima

FOREIGN PATENT DOCUMENTS

JP 2007-189973 A 8/2007
JP 2009102270 A * 5/2009
JP 2010-263816 A 11/2010
WO 2009/138092 A1 11/2009

OTHER PUBLICATIONS

E. Naito, Y. Yoshida, K. Makino, Y. Kounoshi, S. Kunihiro, R. Takahashi, T. Matsuzaki, K. Miyazaki and F. Ishikawa, Beneficial effect of oral administration of Lactobacillus casei strain Shirota on insulin resistance in diet-induced obesity mice, 2011, J. Appl. Microbiol., vol. 110, pp. 650-657 (Year: 2011).*
I Kato, S Kobayashi, T Yokokura, M Mutai, Antitumor activity of Lactobacillus casei in mice, 1981, Gan., vol. 72, No. 4, pp. 517-523 (Abstract only) (Year: 1981).*
Annika Nerstedt, et al., "Administration of Lactobacillus Evokes Coordinated Changes in the Intestinal Expression Profile of Genes Regulating Energy Homeostasis and Immune Phenotype in Mice," British Journal of Nutrition, vol. 97, 2007, pp. 1117-1127. (11 pages total).
Chakradhar V. Lagishetty et al., "Polyamines: Potential anti-inflammatory agents and their possible mechanism of action", Indian J. Pharmacol., Jun. 2008, pp. 121-125, vol. 40, No. 3.
Communication, dated Oct. 2, 2017, from the European Patent Office in counterpart application No. 15770338.0.
E. Cario et al., "Toll-Like Receptor 2 Controls Mucosal Inflammation by Regulating Epithelial Barrier Function", Gastro Enterology, 2007, pp. 1359-1374, vol. 132, No. 4.
Elin Chorell, et al., "Impact of Probiotic Feeding During Weaning on the Serum Lipid Profile and Plasma Metabolome in Infants," British Journal of Nutrition, vol. 110, Dec. 11, 2012, pp. 116-126. (11 pages total).
Francois-Pierre J. Martin, et al., "Effects of Probiotic Lactobacillus Paracasei Treatment on the Host Gut Tissue Metabolic Profiles Probed via Magic-Angle-Spinning NMR Spectroscopy," Journal of Proteome Research Articles, vol. 6, Feb. 23, 2007, pp. 1471-1481. (11 pages total).
Harutoshi Tsuda et al., "Isolation and Identification of Lactic Acid Bacteria in Traditional Fermented Sushi, Funazushi, from Japan", Food Sci. Technol. Res., 2012, pp. 77-82, vol. 18, No. 1.
International Search Report of PCT/JP2015/058750, dated May 19, 2015.
Jordi Folch et al., "A Simple Method for the Isolation and Purification of Total Lipids From Animal Tissues", J. Biol. Chem., 1957, pp. 497-509, vol. 226, No. 1.

(Continued)

*Primary Examiner* — David W Berke-Schlessel
*Assistant Examiner* — Trent R Clarke
(74) *Attorney, Agent, or Firm* — Sughrue Mion, PLLC

(57) ABSTRACT

The present disclosure relates to a *Lactobacillus paracasei* strain having polyamine production promoting activity in an organism, as well as its application and relevant technologies. The present disclosure also relates to the use of the *Lactobacillus paracasei* strain to promote polyamine production in humans and animals, which may be used, for instance, to reduce hepatic neutral fat. The present disclosure also relates to the use of the *Lactobacillus paracasei* strain as an agent to prevent or treat a disease, including fatty liver, non-alcoholic steatohepatitis, and liver cirrhosis.

6 Claims, No Drawings

(56) References Cited

OTHER PUBLICATIONS

Karl J. Kaiyala et al., "Direct animal calorimetry, the underused gold standard for quantifying the fire of life", Comparative Biochemistry and Physiology, Part A, 2011, pp. 252-264, vol. 158.

Khaider K Sharafedtinov et al., "Hypocaloric diet supplemented with probiotic cheese improves body mass index and blood pressure indices of obese hypertensive patients—a randomized double-blind placebo-controlled pilot study", Nutrition Journal, 2013, pp. 1-11, vol. 12, No. 138.

Kuniyasu Soda et al., Polyamine intake, dietary pattern, and cardiovascular disease, Medical Hypotheses pp. 299-301, 2010, vol. 75, No. 3.

L. Geurts, et al., "Gut Microbiota Controls Adipose Tissue Expansion, Gut Barrier and Glucose Metabolism: Novel Insights into Molecular Targets and Interventions Using Prebiotics," Beneficial Microbes, vol. 5, No. 1, Mar. 2014, pp. 3-17. (16 pages total).

Masaya Sasaki et al., "Measurement of resting energy expenditure and substrates expenditure using Indirect Calorimetry", 2009, pp. 1021-1025, vol. 24, No. 5.

Nathalie M. Delzenne, et al., "Targeting Gut Microbiota in Obesity: Effects of Prebiotics and Probiotics," Nature Reviews, Endocrinology, vol. 7, 2011, pp. 629-646. (8 pages).

Olivier Peulen et al., "The relationship between spermine content of human milk during the first postnatal month and allergy in children", Public Health Nutrition, 1998, pp. 181-184, vol. 1, No. 3.

S Klaus et al., "Epigallocatechin gallate attenuates diet-induced obesity in mice by decreasing energy absorption and increasing fat oxidation", International Journal of Obesity, 2005, pp. 615-623, vol. 29.

Taina Koponen et al., "The activation of hepatic and muscle polyamine catabolismimproves glucose homeostasis", Amino Acids, 2012, pp. 427-440, vol. 42, Nos. 2-3.

Tobias Eisenberg et al., "Induction of autophagy by spermidine promotes longevity", Nature Cell Biology, pp. 1305-1314, Nov. 2009, vol. 11, No. 11.

Yukimasa Tanaka-Azuma et al., "Hypocholesterolemic Activity in Lactic Acid Bacteria Isolated from Funazushi", Nippon Shokuhin Kagaku Kogaku Kaishi, pp. 177-183, vol. 56, No. 3.

Kondo Hidehiko et al., "Differential regulation of intestinal lipid metabolism-related genes in obesity-resistant A/J vs. obesity-prone C57BL/6J mice", Am. J. Physiol. Endocrinol. Metab., 2006, pp. E1092-E1099, vol. 291.

Matsuzaka et al., Endocrine Journal, 1997, 44(3), 357-365.

ATCC Catalogue, accessed Aug. 4, 2017, http://www.atcc.org/Search_Results.aspx?dsNav=Ntk:PrimarySearch%7cparacasei%7c3%,Ny:True,Ro:0,N:1000552&searchTerms=paracasei&redir=1.

Tanida et al., Obesity Research & Clinical Practice (2008) 2, 159-169.

\* cited by examiner

LACTOBACILLUS PARACASEI STRAIN

CROSS-REFERENCE TO RELATED APPLICATION

This application is a continuation of U.S. patent application Ser. No. 15/127,301, filed Sep. 19, 2016, which is a National Stage entry of PCT/JP2015/058750, filed Mar. 23, 2015, which claims priority to JP2014-060010, filed Mar. 24, 2014, the contents of all of which are incorporated herein by reference in their entirety.

TECHNICAL FIELD

The present invention relates to a novel *Lactobacillus paracasei* strain (strain WON0604: FERM BP-11468) having polyamine production promoting activity in an organism, as well as its application and relevant technologies.

BACKGROUND ART

Polyamine is a general name for aliphatic hydrocarbons having two or more primary amino groups. Typical examples of polyamine include putrescine, spermidine, spermine, and the like. Polyamine is synthesized in the cells of all organisms, and is involved in cell differentiation or proliferation. In addition to these activities, there are recent reports that polyamine has various helpful physiological activities, including an anti-aging effect (Non-patent Document 1), arteriosclerosis progression retardation activity (Non-patent Document 2), acute and chronic inflammation suppressing activity (Non-patent Document 3), neutral fat reducing activity, insulin resistance alleviating activity, anti-obesity activity, cholesterol level decreasing activity, basal metabolism increasing activity (Non-patent Document 4), and antiallergic activity (Non-patent Document 5).

Polyamine biosynthesis occurs in all animals, including humans; however, this synthesis ability decreases with aging. Therefore, in order to receive the helpful physiological activity of polyamine over a lifetime, there have been discussions regarding external administration or intake of polyamine, or activation of polyamine synthesis ability in an organism.

To date, several food and drinks containing polyamine have been suggested. For example, Patent Document 1 discloses food and drinks containing polyamine extracted from various plant/animal-originated raw materials. Such food and drinks are expected to promote polyamine synthesis in organisms (in particular, in humans), and thereby provide the aforementioned various helpful physiological activities, such as an anti-aging effect, arteriosclerosis progression retardation activity, acute and chronic inflammation suppressing activity, neutral fat reducing activity, insulin resistance alleviating activity, anti-obesity activity, cholesterol level decreasing activity, basal metabolism increasing activity or antiallergic activity. Further, such food and drinks are expected to act, for example, on the improvement, retainment or homeostasis of biomarkers or the like relevant to the above physiological activities, or on prevention of development of diseases.

CITATION LIST

Patent Documents

Patent Document 1: JP2010-263816A

Non-Patent Documents

Non-patent Document 1: Eisenberg T. et al., Nat Cell Biol 2009; 11 (11): 1305-1314
Non-patent Document 2: Soda K., Med. Hypotheses, 2010; 75 (3): 299-301
Non-patent Document 3: Lagishetty C. V. et al., Indian J. Pharmacol. 2008; 40 (3): 121-125
Non-patent Document 4: Koponen T. et al., Amino Acids 2012; 42 (2-3): 427-40.
Non-patent Document 5: Peulen O. et al., Public Health Nutr. 1998; 1 (3): 181-184

SUMMARY OF INVENTION

Technical Problem

An object to be attained by the present invention is to provide an effective means for promoting polyamine synthesis in organisms (in particular, in human organisms).

Solution to Problem

In an attempt to attain the above object, the inventors of the present invention found, among the microorganisms belonging to *Lactobacillus paracasei*, a microorganism capable of promoting polyamine production in human or animal organisms. The inventors of the present invention found that this microorganism has polyamine production promoting activity in the small intestine, as well as hepatic neutral fat reducing activity and/or energy metabolism promoting activity.

Representative examples of the present invention are detailed below.

Item 1.
*Lactobacillus paracasei* strain WON0604 (FERN BP-11468).
Item 2.
*Lactobacillus paracasei* strain WON0604 according to Item 1, further having hepatic neutral fat reducing activity.
Item 3.
*Lactobacillus paracasei* strain WON0604 according to Item 1 or 2, further having energy metabolism promoting activity.
Item 4.
A composition to which *Lactobacillus paracasei* strain WON0604 according to any one of Items 1 to 3 has been added.
Item 5.
The composition according to Item 4, wherein the composition is a polyamine production promoter.
Item 6.
An agent for preventing or treating at least one disease selected from the group consisting of fatty liver, non-alcoholic steatohepatitis, and liver cirrhosis, the agent comprising the *Lactobacillus paracasei* according to Item 2.
Item 7.
An agent for reducing hepatic neutral fat, comprising the *Lactobacillus paracasei* according to Item 2.

Item 8.

A method for promoting polyamine production in a human in need of polyamine production enhancement, comprising administering *Lactobacillus paracasei* strain WON0604 according to any one of Items 1 to 3 to the human.

Item 9.

A method for treating or alleviating a fatty liver patient, comprising administering *Lactobacillus paracasei* strain WON0604 according to Item 2 to the fatty liver patient.

Item 10.

Use of the *Lactobacillus paracasei* according to Item 2 for the manufacture of an agent for preventing and/or treating fatty liver.

Advantageous Effects of Invention

*Lactobacillus paracasei* strain WON0604 (FERM BP-11468; this strain may hereinafter also be referred to as "the microorganism of the present invention") of the present invention has polyamine production promoting activity in organisms of human or other animals. In the present invention, this activity is referred to as "polyamine production promoting activity." By using the microorganism of the present invention (for example, through ingestion or administration), it is possible to promote polyamine production in a human or animal organism. Consequently, the invention enables a human or an animal to effectively receive helpful physiological activities of polyamine (for example, an anti-aging effect, arteriosclerosis progression retardation activity, acute and chronic inflammation suppressing activity, neutral fat reducing activity, insulin resistance alleviating activity, anti-obesity activity, cholesterol level decreasing activity, basal metabolism increasing activity, antiallergic activity, and/or immunostimulatory activity, etc.).

Further, the microorganism of the present invention has hepatic neutral fat reducing activity. Therefore, by using the microorganism of the present invention, it is possible to decrease the hepatic neutral fat level (for example, the amount of the neutral fat accumulated in the liver). The microorganism of the present invention is effective for the retainment or improvement of hepatic lipid metabolism, or prevention or treatment of fatty liver, non-alcoholic steatohepatitis (NASH), and/or liver cirrhosis. Further, the microorganism of the present invention is expected to have an effect of preventing the progression of these diseases into liver cancers, or an effect of preventing the development of cardiovascular diseases.

The microorganism of the present invention has energy metabolism promoting activity in an organism. Therefore, use of the microorganism of the present invention is effective for health maintenance of humans or animals, including suppression of body weight gain, suppression of obesity, reduction in body fat, reduction in visceral fat, and/or prevention of metabolic syndrome. Further, the microorganism of the present invention is expected to have an effect on improvement or retainment of biomarkers relevant to the above physiological activities.

In addition, since the microorganism of the present invention belongs to *Lactobacillus paracasei*, which have been applied in the food field, the microorganism of the present invention is believed to be sufficiently safe as an additive for food compositions. As is thus evident, the microorganism of the present invention is suitable for the fields of food and drinks and/or pharmaceuticals for humans or other animals.

DESCRIPTION OF EMBODIMENTS

1. Microorganism
1-1. Polyamine Production Promoting Activity

The microorganism of the present invention has polyamine production promoting activity. As described above, "polyamine production promoting activity" is an action of promoting polyamine production in organisms of humans or other animals.

The "polyamine" used in the present invention is generally a collective name for aliphatic hydrocarbons having two or more primary amino groups, which is a substance recognized as polyamine. Examples of polyamine include putrescine, spermidine and spermine. The polyamine production promoting activity of the microorganism of the present invention promotes production of at least one kind or two kinds, more preferably all kinds of polyamine. The cells, tissues, and organs in which polyamine production (i.e., polyamine synthesis in the organism) is promoted by the microorganism of the present invention are not particularly limited. Examples of the organs include oral cavity, esophagus, stomach, duodenum, cecum, small intestine, and large intestine, which are organs in which the microorganism orally administered directly takes effect. Small intestine is particularly preferable.

The polyamine production promoting activity of the microorganism of the present invention can be measured using a known analysis technique. Specifically, the polyamine production promoting activity of the microorganism of the present invention can be measured in the following manner using a model animal (for example, mice). More specifically, mice are fed with the microorganism of the present invention for a certain period of time, then their visceral tissues were isolated, and the polyamine amounts in the tissues are measured. Further, the measured polyamine amounts are compared with the polyamine amounts in the visceral tissues isolated from mice that have not been fed with the microorganism of the present invention, thereby measuring a relative increase by the microorganism of the present invention. In this measurement, the sample used for the polyamine amount measurement is not particularly limited. It is, however, preferable to measure and compare the polyamine amounts in the small intestine tissue and the cecal content. For example, when the measurement reveals that the polyamine amount in the small intestine increased whereas the polyamine amount in the cecum content did not increase, it can be judged that the microorganism has an action of promoting polyamine production in an organism.

It is preferable that the polyamine amount in the organism be increased by a factor of 1.1 to 1.5 by the administration of the microorganism of the present invention to humans or other animals, compared with that before the administration. This is, for example, to receive an effect of reducing an increase in hepatic neutral fat by suppressing excessive lipid accumulation or promoting lipid metabolism in the organism.

1-2. Mycological Characteristics

The microorganism of the present invention belongs to *Lactobacillus paracasei*. Table 1 below shows preferable mycological properties of the microorganism.

TABLE 1

| Shape of cell | Rod shape |
| Gram staining | Positive |
| Motility | None |
| Spore | None |

TABLE 1-continued

|  |  |
|---|---|
| Growth temperature | 30-40° C. |
| Growth under anaerobic condition | Positive |
| Growth under aerobic condition | Positive |
| Gas Production | None |

1-3. Characteristics Regarding Colony Formation

The microorganism of the present invention preferably forms colonies having the characteristics below when the microorganism is cultured in agar medium having the formulation below (Lactobacilli MRS Agar #288210) at 37° C. for 16 hours under an anaerobic condition.

| Medium Formulation (pH 6.5 ± 0.2) | |
|---|---|
| Proteose Peptone No. 3 | 10 g |
| Beef extract | 10 g |
| Yeast extract | 5 g |
| Glucose | 20 g |
| Polysorbate 80 | 1 g |
| Ammonium citrate | 2 g |
| Sodium acetate | 5 g |
| Magnesium sulfate | 0.1 g |
| Manganese sulfate | 0.05 g |
| Dipotassium phosphate | 15 g |
| Agar | 15 g |
| Water | 1000 ml |

Colony Form
  Diameter: 1 to 2 mm
  Color: white
  Shape: circular
  State of elevation: convex
  Margin: entire
  Form of surface: smooth
  Transparency: translucent
  Viscosity: butyrous 1-4. Characteristics Regarding Hydrocarbon Assimilation The hydrocarbon assimilation of the microorganism of the present invention is preferably as shown in Table 2 below.

TABLE 2

| Hydrocarbon | Presence/Absence of Assimilation |
|---|---|
| Glycerol | − |
| Erythritol | − |
| D-arabinose | − |
| L-arabinose | − |
| D-ribose | + |
| D-xylose | − |
| L-xylose | − |
| D-adonitol | + |
| Methyl-β-D-xylopyranoside | − |
| D-galactose | + |
| D-glucose | + |
| D-fructose | + |
| D-mannose | + |
| L-sorbose | + |
| L-rhamnose | − |
| Dulcitol | − |
| Inositol | − |
| D-mannitol | + |
| D-sorbitol | + |
| Methyl α-D-mannopyranoside | − |
| Methyl α-D-glucopyranoside | + |
| N-acetylglucosamine | + |
| Amygdalin | + |
| Arbutin | + |
| Esculin Ferric Citrate | + |
| Salicin | + |
| D-cellobiose | + |
| D-maltose | + |
| D-lactose | + |
| D-melibiose | − |
| D-sucrose | + |
| D-trehalose | + |
| D-inulin | − |
| D-melezitose | + |
| D-raffinose | − |
| Starch | − |
| Glycogen | − |
| Xylitol | − |
| Gentiobiose | + |
| D-turanose | + |
| D-lyxose | + |
| D-tagatose | + |
| D-fucose | − |
| L-fucose | − |
| D-arabitol | − |
| L-arabitol | − |
| Gluconate | + |
| 2-ketogluconate | − |
| 5-ketogluconate | − |

In the table, "+" means positive, and "−" means negative.

1-5. Hepatic Neutral Fat Reducing Activity

The microorganism of the present invention preferably has hepatic neutral fat reducing activity when it is ingested by or administered to humans or other animals. The neutral fat is not particularly limited, but is generally triglyceride. Since the hepatic neutral fat reducing activity of the microorganism of the present invention makes it possible to reduce the amount of neutral fat already accumulated in the liver, the microorganism of the present invention is useful for, for example, treatment or alleviation of humans having fatty liver, as well as prevention of progression of fatty liver in humans with a risk of fatty liver, or health maintenance. Further, the microorganism of the present invention is also useful for prevention of progression to NASH, liver cirrhosis, liver cancer, and/or heart disease due to hepatic neutral fat accumulation.

The hepatic neutral fat reducing activity of the microorganism of the present invention may be measured using a known analysis technique. Specifically, the hepatic neutral fat reducing activity of the present invention may be measured using a model animal (for example, mice) according to the procedures below. Mice are fed with the microorganism of the present invention for a certain period of time; thereafter, their livers are isolated and neutral fats are extracted according to the method of Folch et al. (J. Biol. Chem. 1957; 226 (1):497-509). The amounts of the neutral fats are measured using a kit obtained from a commercial supplier. With the same procedures, the amounts of neutral fats in the livers isolated from mice that have not been fed with the microorganism of the present invention are measured. Then, the neutral fat amounts in the mice fed with the microorganism of the present invention are compared with the neutral fat amounts in the mice unfed with the microorganism of the present invention, thereby measuring the hepatic neutral fat reducing activity.

1-6. Energy Metabolism Promoting Activity

The microorganism of the present invention preferably has energy metabolism promoting activity in an organism when it is ingested by or administered to humans or other animals. More specifically, the microorganism of the present invention has an action of promoting energy metabolism in the intestinal tissue (in particular, in the small intestinal tissue) and/or liver. By using the microorganism of the present invention, it is possible to improve constitutions, or alleviate metabolic syndrome and/or obesity or the like of humans or other animals in need of energy metabolism promotion.

As shown in the Examples, the energy metabolism promoting activity of the microorganism of the present invention may be confirmed by measuring changes in expression amounts of mRNA encoding energy metabolism-related enzymes (Kondo et al., Am. J. Physiol. Endocrinol Metab, 291, E1092-E1099, 2006). In addition, the energy metabolism promoting activity of the microorganism of the present invention may be confirmed by calorimetric measurement in humans or other animals before and after the intake of the microorganism of the present invention (Sasaki, Measurement of resting energy expenditure and substrates expenditure using Indirect calorimetry, 24, 5, 1021-1025; Kaiyala et al., Comparative Biochemistry and Physiology, Part A 158, 252-264, 2011), measurements of oxygen intake amount and carbon dioxide output (Klaus et al., International Journal of Obesity, 29, 615-623, 2005), and/or measurements of the activities of metabolism-related enzymes.

1-7. Other Activities

In addition to the above, the microorganism of the present invention preferably also has blood glucose level reducing activity, blood neutral fat level reducing activity, blood endotoxin level reducing activity, selective saturated fatty acid reducing activity, fatty acid β oxidation promoting activity in the small intestine and the liver, and/or TLR-2m RNA expression promoting activity in the small intestine, and the like. Accordingly, the microorganism of the present invention is useful for the treatment of diabetes patients based on its blood glucose level reducing activity, and is also useful for the treatment of septicemia based on its blood endotoxin level reducing activity. Further, the fatty acid β oxidation promoting activity in the small intestine and the liver is conducive to the energy metabolism promotion mentioned above. Further, since TLR-2m RNA expression in the small intestine increases the barrier function of the small-intestinal mucosa, and thereby brings about immuno-stimulatory activity (Cario et al., Gastroenterology, 132, 4, 1359-1374, 2007), the effects on the prevention or treatment of inflammatory bowel disease, bacterial infection, virus infection, endotoxemia, heart disease, atherosclerosis, food allergy, atopic dermatitis, and like are expected.

1-8. Representative Strain

The representative microorganism of the present invention is strain WON0604. This strain was internationally deposited with the International Patent Organism Depositary, National Institute of Advanced Industrial Science and Technology (Central 6, 1-1-1 Higashi, Tsukuba, Ibaraki 305-8566 Japan) on Feb. 20, 2012, under accession No. FERM BP-11468. Strain WON0604 satisfies all of the above characteristics 1-1 to 1-7. The International Patent Organism Depositary in the National Institute of Advanced Industrial Science and Technology was consolidated with the International Patent Organism Depositary in the Incorporated Administrative Agency National Institute of Technology and Evaluation (NITE) on April 2012, and their responsibility regarding Patent Organism Depositary was taken over by the International Patent Organism Depositary in the Biological Resource Center of the National Institute of Technology and Evaluation (NITE-IPOD) (Room 120 2-5-8 Kazusa-Kamatari, Kisarazu-city, Chiba 292-0818 JAPAN).

The microorganism of the present invention is preferably in an isolated state. Further, insofar as the polyamine production promoting activity, the hepatic neutral fat reducing activity and the energy metabolism promoting activity described above are ensured, the microorganism of the present invention may be viable cells or dead cells, and may be in a state of purified cells, roughly purified cells, cells mixed with unpurified medium, or a cell extract. The microorganism of the present invention is preferably viable cells because viable cells continuously and effectively exhibit polyamine production promoting activity in an organism. Further, by adding a commonly used freeze-dried preservative to viable cells to freeze-dry the cells, and conserving the resulting freeze-dried cells in a refrigerator or in a freezer, it becomes possible to conserve the viable cells for a long period of time. In one embodiment, the microorganism of the present invention is in a freeze-dried state.

1-9. Method for Obtaining the Microorganism of the Present Invention

The source from which the microorganism of the present invention is to be isolated is not particularly limited. For example, the microorganism of the present invention may be isolated from foods known to contain *Lactobacillus paracasei* therein (for example, various Japanese pickles, Korean pickles, cow's milk, cheese, and the like). Since *Lactobacillus paracasei* strain WON0604, i.e., the microorganism of the present invention, was isolated using Crucian carp sushi as a source, the microorganism of the present invention may, for example, be isolated using Crucian carp sushi as a source. Crucian carp sushi designates a food produced by lactic fermentation of rice and fish produced around Lake Biwa in Japan. The isolation of lactic acid bacteria from Crucian carp sushi may be conducted, for example, according to the method disclosed in Tuda et al. (Food Sci. Technol. Res., 18 (1), 77-82, 2012).

The isolation of the microorganism of the present invention may be performed by a known screening method using polyamine production promoting activity, hepatic neutral fat reducing activity, and energy metabolism promoting activity described above as indices. For example, the microorganism of the present invention may be isolated by (1) confirming whether the food or the like used as the source has polyamine production promoting activity, (2) diluting the source which had its polyamine production promoting activity confirmed with an appropriate buffer solution, applying the diluted source to agar medium to culture the cells into colonies, (3) identifying a colony or colonies having polyamine production promoting activity among the colonies formed, (4) extracting 16Sr DNA from the colony, thereby determining the sequence thereof, and thereby judging whether the source belongs to *Lactobacillus paracasei*.

2. Composition

The composition of the present invention is a composition to which the microorganism of the present invention has been added. The type and the form of the composition are not particularly limited insofar as the polyamine production promoting activity and, preferably, the hepatic neutral fat reducing activity and the energy metabolism promoting activity of the microorganism of the present invention, are not inhibited. However, in view of desirable exhibition of these functions in animals, in particular, in human organisms, the composition is preferably a food or beverage composition, or a pharmaceutical composition.

With the addition of the microorganism of the present invention, the composition of the present invention has polyamine production promoting activity, hepatic neutral fat reducing activity, and/or energy metabolism promoting activity. Therefore, in a preferred embodiment, it is possible to use the composition of the present invention for a polyamine production promoter, a hepatic neutral fat reducer, and/or an energy metabolism promoter. Although the above polyamine production promoter and the like may be in the form of a composition, it may also consist only of the microorganism of the present invention.

The composition of the present invention may contain other arbitrary components according to its form and purpose, insofar as the polyamine production promoting activity and the like of the microorganism of the present invention are not interfered. For example, in view of maintaining the growth of the microorganism of the present invention, the composition of the present invention preferably contains, for example, nutrient compositions suitable for the growth of the microorganism of the present invention, such as skim milk, dextrin, and the like.

The amount of the microorganism of the present invention to be added to the composition of the present invention is not particularly limited, and may be suitably set insofar as the polyamine production promoting activity and the like of the microorganism are exhibited in animals, in particular, in human organisms. For example, on a viable cell basis, the composition of the present invention may contain the microorganism in an amount of about $1.0 \times 10^4$ to $1.0 \times 10^{16}$ CFU per gram of the composition, preferably $1.0 \times 10^6$ to $1.0 \times 10^{14}$ CFU per gram of the composition, more preferably $1.0 \times 10^8$ to $1.0 \times 10^{12}$ CFU per gram of the composition.

The type or the form of the food or beverage composition to which the microorganism of the present invention is added is not particularly limited, and examples include, in addition to general food and drinks, various functional foods (e.g., food for specified health use, dietary supplement, supplement, patient food, and health food). By adding the microorganism of the present invention to such foods, it is possible to further improve the polyamine production promoting activity and the like, and thereby provide an improved food or beverage composition that more efficiently promotes polyamine production in an organism. Such an improved food or beverage composition may also be used for homeostatic control in an organism.

When the composition of the present invention is a food or beverage composition, the form of the composition is not particularly limited insofar as the polyamine production promoting activity and the like of the microorganism of the present invention are not inhibited. Examples of food composition include granules, fine granules, powder, capsules, tablets, gum, jelly, gummy candy, bars, chips, flakes and other general foods. Examples of general foods include chocolates, biscuits, candies, cookies, tablet confectioneries, ice cream, sherbet, Udon (wheat) noodles, soba (buckwheat) noodles, pasta, and somen (thin wheat) noodles. Examples of drink compositions include various drinks such as powder drinks, soft drinks, milk beverages, nutritional beverages, carbonated drinks, and jelly drinks. Examples of the forms of functional food include powder, granules, capsules, syrup, tablets, sugar-coated tablets, and sublingual tablets.

The means for adding the microorganism of the present invention to a food or beverage composition is not particularly limited. For example, the microorganism of the present invention may be added to a food or beverage composition during the manufacture, processing, or in a final step of the food or beverage composition, by way of addition, mixing, infiltration or the like. Further, the microorganism of the present invention may be added in the form of powder, granules, capsules, syrup, tablets or the like upon intake of food and drinks.

When the composition of the present invention is a pharmaceutical composition, it is possible to produce various drug forms by mixing the microorganism of the present invention with a pharmaceutically acceptable carrier. The pharmaceutically acceptable carrier is not particularly limited insofar as the polyamine production promoting activity and the like of the microorganism of the present invention are not inhibited. Examples of pharmaceutically acceptable carriers include various fillers, expanders, binders, moisturizers, disintegrants, surface active agents, lubricants, and diluents, which are generally used in the medical field. The form of the pharmaceutical composition in which the microorganism of the present invention is added is not particularly limited. Examples of the form include tablets, pills, powdered drug, liquids, suspensions, emulsions, granules, and capsules. The drug form is preferably a form suitable for oral administration.

By containing the microorganism of the present invention, the pharmaceutical composition of the present invention exhibits polyamine production promoting activity as well as, preferably, hepatic neutral fat reducing activity and energy metabolism promoting activity. Therefore, the pharmaceutical composition of the present invention may be used as a pharmaceutical composition for promoting polyamine production in an organism, a pharmaceutical composition for reducing hepatic neutral fat, and/or a pharmaceutical composition for promoting energy metabolism. Further, based on the hepatic neutral fat reducing activity of the microorganism of the present invention, the pharmaceutical composition of the present invention may be used as a pharmaceutical composition for the prevention or treatment of fatty liver, a pharmaceutical composition for the prevention of progression or the treatment of NASH, liver cirrhosis, and/or liver cancer. Additionally, based on the energy metabolism promoting activity of the microorganism of the present invention, the pharmaceutical composition of the present invention may be used as a pharmaceutical composition for the prevention or treatment of metabolic syndrome.

The amount of the microorganism of the present invention to be added to the pharmaceutical composition of the present invention is similar to the amount defined above for general compositions. The dose of the pharmaceutical composition of the present invention may be suitably set according to the symptom, age, weight and the like of the human or the animal who intakes the composition.

The dosage form of the pharmaceutical composition of the present invention is not particularly limited, insofar as the polyamine production promoting activity and the like of the microorganism of the present invention are exhibited in the body. However, the dosage form is preferably oral administration.

3. Treatment and Alleviation Method

The microorganism of the present invention has polyamine production promoting activity in an organism of animals, in particular, humans. Polyamine is known to have an anti-aging effect, arteriosclerosis progression retardation activity, acute and chronic inflammation suppressing activity, neutral fat reducing activity, insulin resistance alleviating activity, anti-obesity activity, cholesterol level decreasing activity, basal metabolism increasing activity, antiallergic activity, immunostimulatory activity, and the like. Therefore, a method for preventing, treating, or alleviating various diseases using these activities, comprising administering the microorganism of the present invention, may be provided. Further, in a preferred embodiment, the microorganism of the present invention has hepatic neutral fat reducing activity. Therefore, by administering the microorganism of the present invention to a human or an animal in need of reduction in hepatic neutral fat, it is possible to reduce the hepatic neutral fat. Further, in a preferred embodiment, the present invention has energy metabolism promoting activity in an organism. Therefore, by administering the microorganism of the present invention to a human or an animal in need of promotion of energy metabolism, it is possible to suppress body weight gain, suppress obesity, reduce body fat, reduce visceral fat, and prevent, alleviate, or treat metabolic syndrome.

The dose of the microorganism of the present invention, or the dose of the pharmaceutical composition of the present invention in which the microorganism of the present invention is added in order to carry out the above method may be suitably set according to the symptom or the like of the patient. For example, the dose is $1.0 \times 10^5$ to 1.0 to $10^{15}$ CFU/kg/day.

EXAMPLES

Example 1

Isolation of Microorganism 0.8 to 1.0 g of homogenized Crucian carp sushi was placed in a 15 ml centrifuge tube, and ten times the amount of physiological saline solution was added and stirred. 1 ml of the stirred suspension was removed and placed in a 15 ml centrifuge tube together with 9 ml of a physiological saline solution, followed by stepwise dilution. 100 µl of each diluent was obtained, inoculated into MRS agar medium, and cultured for 24 hours at 37° C. under an anaerobic condition. After the culture, the cells were purified until they became a single colony. These operations were performed as aseptic manipulation.

The isolated strain WON0604 was deposited with the International Patent Organism Depositary, National Institute of Advanced Industrial Science and Technology (1-1-1 Higashi, Tsukuba-city, Ibaraki 305-8566 Japan), under accession No. FERM BP-11468.

Example 2

Polyamine Production Promoting Activity

KK-Ay mice (type II diabetes model, male) at 4 weeks of age were fastened for 16 hours, and blood was drawn from a single capillary vessel in the tail vein (about 75 µl). Plasma was prepared by centrifugation (12,000 rpm (15,000×g)×5 minutes), and the blood glucose concentration and the blood neutral fat concentration were measured. Mice with no abnormal health conditions were classified into a control group and a test group, while eliminating bias in body weight (the day before the grouping) and blood glucose concentration by way of stratified random sampling using SAS software (R9.1, SAS Institute Japan). For 28 days, the control group was freely fed with a control meal (AIN-93G), and the test group was freely fed with a test meal mixed with strain WON0604 at a proportion of $1.0 \times 10^9$ CFU/day (viable cells). Thereafter, the cecum and the small intestine tissue were dissected, and the polyamine concentrations in the cecal content and the small intestine tissue were measured. Table 3 shows the values of each test group relative to the polyamine concentration of the control group, which is assumed as 1. n=3 both for the cecal content and the small intestine tissue. The polyamine concentration in the cecal content was measured by an on-column derivatization method using O-phthalaldehyde. The polyamine concentration in the small intestine tissue was measured using a CE-TOFMS system (Agilent Technologies). The significance test was performed according to Welch's t-test.

TABLE 3

Polyamine amount in small intestine

|  | Relative value against control | P Value |
|---|---|---|
| Putrescine | 1.4 | 0.007* |
| Spermidine | 1.3 | 0.064 |
| Spermine | 1.1 | 0.523 |

*$P < 0.01$

TABLE 4

Polyamine amount in cecum

|  | Relative value against control | P Value |
|---|---|---|
| Putrescine | 0.79 | 0.412 |
| Spermidine | 1.07 | 0.549 |
| Spermine | 0.93 | 0.549 |

As shown in Table 4, the polyamine concentration in the cecum was not increased by the intake of strain WON0604. In contrast, as shown in Table 3, putrescine was significantly increased in the small intestine, and there was also a tendency for spermidine and spermine to increase in the small intestine. The results thus revealed that polyamine in the small intestine was increased by the intake of strain WON0604. This clarified that the microorganism of the present invention has an action of promoting polyamine synthesis capability itself in the small intestine (i.e., polyamine synthesis promoting activity).

Example 3

Energy Metabolism Promoting Activity

Similarly to Example 2, KK-Ay mice (type II diabetes model, male) at 4 weeks of age were classified into a control group and a test group; the control group was freely fed with a control meal (AIN-93G), and the test group was freely fed with a test meal mixed with strain WON0604 at a proportion of $1.0 \times 10^9$ CFU/day (viable cells) for 28 days. Thereafter, mRNA expression levels of various energy metabolism-related enzymes in the liver and the small intestine were measured. The mRNA extraction and purification were performed using a RiboPure® Kit (Ambion). Table 5 shows the results, i.e., the values of the test meal groups relative to the value of the control group, which is assumed as 1. In this test, n=13, and the relative values were calculated using average values.

TABLE 5

|  | Relative mRNA expression level in liver | P Value |
|---|---|---|
| Acox1 | 1.16 | 0.020* |
| Ucp2 | 1.33 | 0.048* |
| Acot2 | 1.29 | 0.058 |

*$P < 0.05$

TABLE 6

| | Relative mRNA expression level in small intestine | P Value |
|---|---|---|
| Acox1 | 1.31 | 0.001* |
| Ucp2 | 1.17 | 0.067 |
| Acot2 | 1.21 | 0.066 |

*P < 0.05

The results shown in Tables 5 and 6 confirmed that the intake of the microorganism of the present invention increased the mRNA expression amounts of Acox1, Ucp2 and Acot2 in the liver and the small intestine. The relevance of the expression of these genes and energy metabolism promotion has been reported by Kondo et al. (Kondo H, et al., Am J Physiol. Endocrinol Metab 2006; 291(5): E1092-9). The results confirmed that, in addition to the polyamine production promoting effect, the possibility of promotion in energy metabolism in the liver and the small intestine by the intake of the microorganism of the present invention was also confirmed.

Example 4

Hepatic Neutral Fat Reducing Activity

Similarly to Example 2, KK-Ay mice (type II diabetes model, male) at 4 weeks of age were classified into a control group and a test group; the control group was freely fed with a control meal (AIN-93G) for 28 days, and each test group was freely fed with a test meal mixed with 3% of a test meal containing strain WON0604, strain WON1052, strain WON1081, or strain WON1033 at a proportion of $1.0 \times 10^9$ CFU/day (viable cells) for 28 days. These lactic acid bacterial strains other than strain WON0604 were obtained by selecting strains resistant to gastric acid and biliary acid through an in vitro test, and then further selecting strains with potential efficacies with respect to blood neutral fat and hepatic neutral fat through an exploratory animal test using KK-Ay mice. Thereafter, the liver was removed from each mouse in a fasted condition. The outer region of the lobus hepatis sinister was weighed, and the lipid fraction was extracted using the method of Folch et al. (Folch J. et al., J. Biol. Chem. 1957; 226(1):497-509) and solubilized using isopropanol; thereafter, the neutral fat concentration was measured using a measurement kit obtained from a commercial supplier (Triglyceride E-test Wako; Wako Pure Chemical Industries, Ltd.). Table 7 shows average values of the measurement results. Each test group had eight mice. The significance test was performed according to t-test.

As shown in Table 7, the hepatic TG concentration was decreased only in the mice fed with strain WON0604, compared with the control group with significant difference; and the hepatic TG concentration reducing activity was not observed in the comparative test groups fed with lactic acid bacteria other than strain WON0604. The results thus confirmed the possibility of hepatic neutral fat reducing activity by the microorganism of the present invention, in addition to the polyamine production promoting effect.

TABLE 7

| | Hepatic TG (mg/g liver) |
|---|---|
| Control group | 29.5 ± 8.5 |
| WON0604 | 18.4 ± 6.8* |
| WON1052 | 26.4 ± 6.3 |
| WON1081 | 34.6 ± 9.0 |
| WON1033 | 25.3 ± 9.7 |

*P < 0.05

Accession Number

FERM BP-11468

The invention claimed is:

1. A method for promoting polyamine production, comprising administering to a human in need thereof an effective amount of a composition comprising *Lactobacillus paracasei* strain WON0604.

2. A method for promoting polyamine production as claimed in claim 1, wherein the composition comprises strain WON0604 in an amount of $1.0 \times 10^4$ to $1.0 \times 10^{16}$ CFU per gram of the composition.

3. A method for promoting energy metabolism, comprising administering to a human in need thereof an effective amount of a composition comprising *Lactobacillus paracasei* strain WON0604.

4. A method for promoting energy metabolism as claimed in claim 3, wherein the composition comprises strain WON0604 in an amount of $1.0 \times 10^4$ to $1.0 \times 10^{16}$ CFU per gram of the composition.

5. A method for reducing neutral fat, comprising administering to a human in need thereof an effective amount of a composition comprising *Lactobacillus paracasei* strain WON0604.

6. A method for reducing neutral fat as claimed in claim 5, wherein the composition comprises strain WON0604 in an amount of $1.0 \times 10^4$ to $1.0 \times 10^{16}$ CFU per gram of the composition.

* * * * *